United States Patent
Holman et al.

(10) Patent No.: US 8,114,153 B2
(45) Date of Patent: Feb. 14, 2012

(54) ENDOPROSTHESES

(75) Inventors: Tom Holman, Princeton, MN (US); Jan Weber, Maastricht (NL); Afsar Ali, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 20 days.

(21) Appl. No.: 12/205,004

(22) Filed: Sep. 5, 2008

(65) Prior Publication Data
US 2010/0063584 A1     Mar. 11, 2010

(51) Int. Cl.
*A61F 2/06* (2006.01)
(52) U.S. Cl. .............. 623/1.44; 623/1.42; 623/1.46
(58) Field of Classification Search .......... 623/1.42, 623/1.44, 1.46
See application file for complete search history.

(56) References Cited

U.S. PATENT DOCUMENTS

| | | | |
|---|---|---|---|
| 5,091,205 A | 2/1992 | Fan | |
| 6,290,721 B1 | 9/2001 | Heath | |
| 6,638,302 B1 * | 10/2003 | Curcio et al. | 623/1.46 |
| 6,979,348 B2 * | 12/2005 | Sundar | 623/1.15 |
| 7,727,273 B2 | 6/2010 | Stinson et al. | |
| 7,947,004 B2 | 5/2011 | Kazerooni et al. | |
| 2002/0144757 A1 | 10/2002 | Craig et al. | |
| 2003/0018380 A1 | 1/2003 | Craig et al. | |
| 2003/0077200 A1 | 4/2003 | Craig et al. | |
| 2004/0143317 A1 | 7/2004 | Stinson et al. | |
| 2005/0019265 A1 | 1/2005 | Hammer et al. | |
| 2005/0070990 A1 | 3/2005 | Stinson | |
| 2005/0216074 A1 | 9/2005 | Sahatjian et al. | |
| 2006/0038027 A1 | 2/2006 | O'Connor et al. | |
| 2006/0173421 A1 | 8/2006 | Weber et al. | |
| 2007/0191923 A1 | 8/2007 | Weber et al. | |
| 2007/0191931 A1 | 8/2007 | Weber et al. | |
| 2008/0145400 A1 | 6/2008 | Weber et al. | |
| 2009/0112310 A1 * | 4/2009 | Zhang | 623/1.42 |
| 2009/0118809 A1 | 5/2009 | Scheuermann et al. | |
| 2009/0118823 A1 | 5/2009 | Atanasoska et al. | |

OTHER PUBLICATIONS

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.
Csete et al., "The existence of sub-micrometer micromechanical modulation generated by polarized UV laser illumination on polymer surfaces," Materials Science and Engineering C, vol. 23, pp. 939-944, (2003).
Csete et al., "The role of original surface roughness in laser-induced periodic surface structure formation process on poly-carbonate films," Thin Solid Films, vol. 453-454, pp. 114-120, (2004).
Lippert et al., "Chemical and Spectroscopic Aspects of Polymer Ablation: Special Features and Novel Directions," Chemical Reviews, vol. 103, pp. 453-485, (2003).
Schetsky, "Shape Memory Alloys", Encyclopedia of Chemical Technology (3rd ed.), John Wiley & Sons, vol. 20, pp. 726-736, (1982).
Wong et al., "Polymer segmental alignment in polarized pulsed laser-induced periodic surface structures," Applied Physics A, vol. 65, pp. 519-523, (1997).

* cited by examiner

*Primary Examiner* — Thomas J Sweet
*Assistant Examiner* — Matthew Schall
(74) *Attorney, Agent, or Firm* — Fish & Richardson P.C.

(57) ABSTRACT

Endoprosthesis assemblies and methods of making endoprosthesis assemblies are disclosed. For example, endoprosthesis assemblies are described that include an endoprosthesis body and a polymeric coating about the endoprosthesis body. The polymeric coatings are engaged tightly to the endoprosthesis wall through engageable features created on the surface of the polymeric coatings and the surface of the endoprosthesis wall prior to engaging the surfaces.

17 Claims, 5 Drawing Sheets

ENDOPROSTHESES

TECHNICAL FIELD

This invention relates to endoprostheses.

BACKGROUND

The body includes various passageways such as arteries, other blood vessels and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

In a first aspect, the invention features a method of making an implantable medical device assembly. The method includes providing a first member having a surface defining a plurality of first engageable features; providing a second member having a surface defining a plurality of second engageable features; pressing the first member with the second member in a manner that first features frictionally engage with second features to provide an assembly; and delivering the assembly into the body.

In an aspect, the invention features an implantable medical device assembly including a first preformed layer having a surface defining a plurality of first engageable features; a second preformed layer having a surface defining a plurality of second engageable features; and an interface between the first and second preformed layers in which the first features frictionally engage with the second features.

In one aspect, the invention features a method of making an implantable medical device assembly. The method includes providing a first member having a surface defining a plurality of first engageable features, providing a second member comprising a polymer material having a surface defining a plurality of second engageable features, pressing the first member with the second member in a manner that first features frictionally engage with second features to provide an assembly, and delivering the assembly into the body.

In another aspect, the invention features an implantable medical device assembly. The assembly includes a first preformed layer having a surface defining a plurality of first engageable features, a second preformed layer having a surface defining a plurality of second engageable features, and an interface between the first and second layers in which the first features frictionally engage with the second features to form said assembly.

Embodiments may include one or more of the following features. The first or second features can be formed by ion bombardment, laser irradiation, or laser ablation. The first feature can be formed by ion bombardment and the second feature can be formed by laser irradiation. The first and second features can be projections having a thickness and width of about 0.5 to 20µ. At least one of the features can be overhanging projections. The first member can be a metal and the second member can be a polymer. The first member can be a stent and the second member can be a layer for positioning over the stent. The first member can be a stent and the second member can be a balloon for expanding the stent.

Embodiments may also include one or more of the following features. At least one of the first or second engageable features can comprise a plurality of overhanging projections. Both the first and second features can have overhanging projections. The projections of the first and second features can have a height and width of about 0.5 to 10 µm. The first layer can comprise a metal. The second layer can be a polymer. Both the first and second layers can be polymer or metal. The polymer material can include a drug. The first layer can be a stent body. The endoprosthesis can be a stent including abluminal and adluminal surface regions, and the first and second layers and the interface can be on the abluminal surface region. The second layer and the interface can be only on the abluminal surface region. The stent can include multiple second layer regions at different locations over the first layer. Second layer regions can carry different drugs or can have different drug delivery profiles. The medical device can be a stent. The medical device can be a stent and delivery balloon.

Embodiments and/or aspects may include any one or more of the following advantages. Implantable medical device assemblies can be provided that include a film tightly bonded to a surface without melting or chemical bonding. For example, endoprostheses can be provided including drug-carrying polymeric films that are engaged tightly to a select surface, e.g. the abluminal surface region of the endoprosthesis wall. Rather than coating a polymer directly on the stent by applying in a solvent or melting, the polymer is provided as a preform, which is pressed onto the stent. The adherence of the polymer to the stent is enhanced by overhanging engaging features on the surface of polymer and the stent. The engaging features can act like hook and loop type fasteners. For example, the metal or polymeric surface of an endoprosthesis can be treated with ion bombardment and/or laser irradiation to create engageable features composed of or enhancing projections. The engagement mechanism can be used with other medical devices. For example, the engagement of the balloon surface and the endoprosthesis adluminal surface can provide a balance of retention and withdrawal forces between the delivered endoprosthesis and the withdrawing catheter balloon. The engagement of the surfaces can be realized by creating engageable features that have similar scales on both the endoprosthesis surface, e.g. by ion bombardment, and the outer surface of the polymeric balloon, e.g. by laser irradiation.

Other features and advantages of the invention will be apparent from the following detailed description, and from the claims.

DESCRIPTION OF DRAWINGS

FIGS. 5A and 5B illustrate regions 5A and 5B in FIGS. 1A and 1B.

DETAILED DESCRIPTION

Figure 1A:
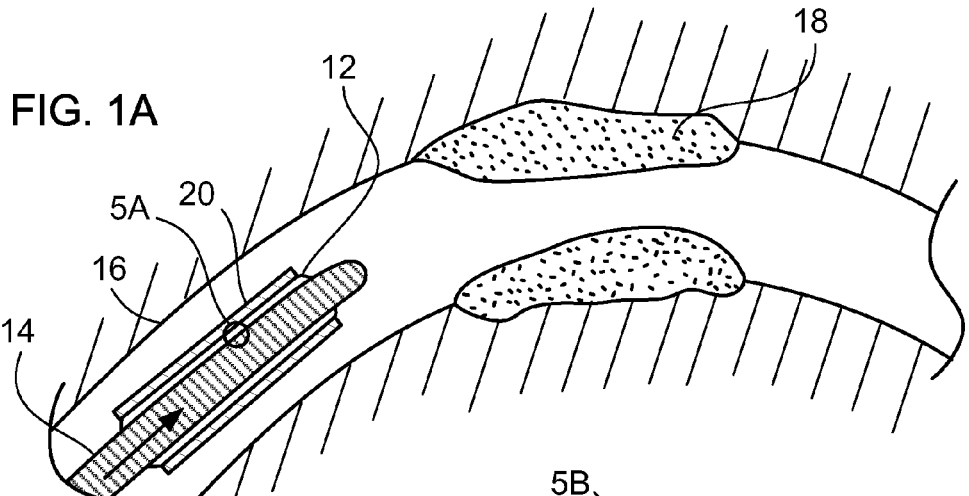
FIGS. 1A-1C are longitudinal cross-sectional views, illustrating delivery of a stent in a collapsed state, expansion of the stent, and deployment of the stent.
Figure 1B:
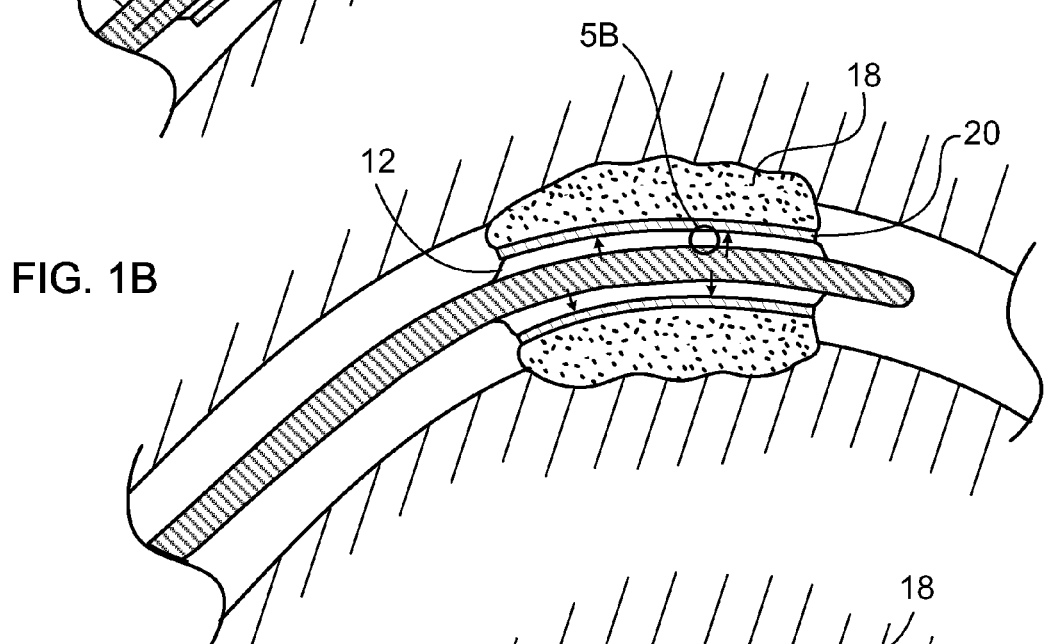
Figure 1C:
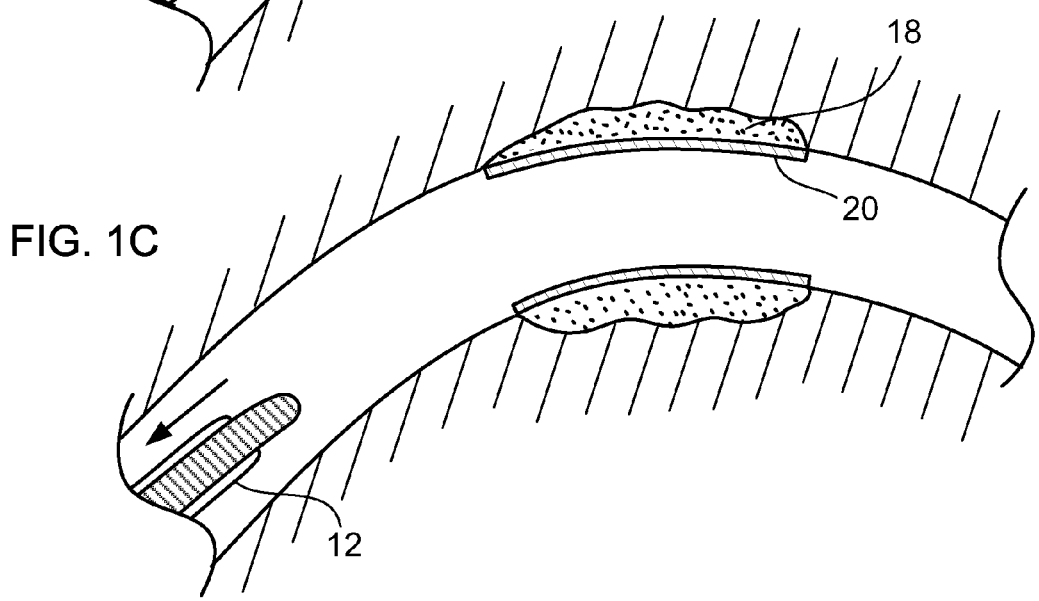

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2:
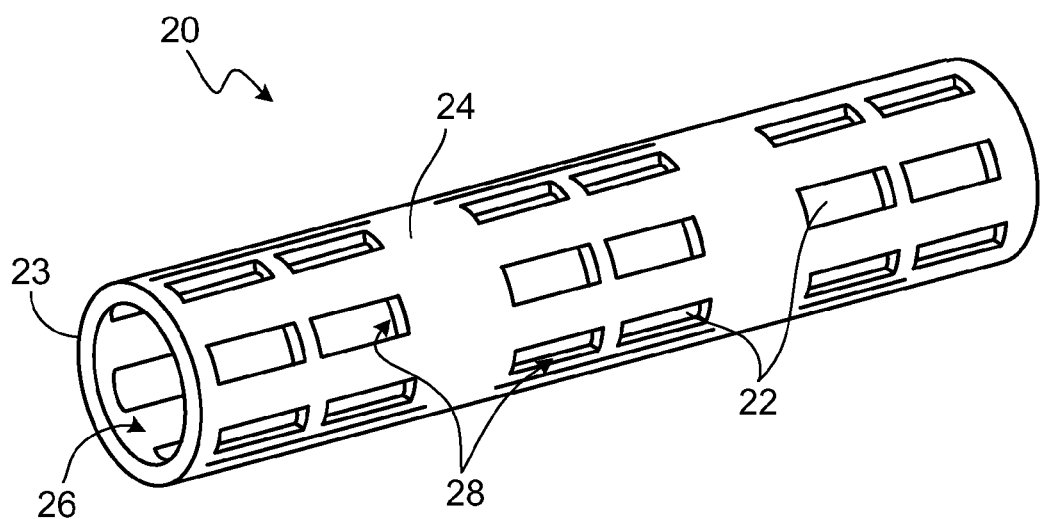
FIG. 2 is a perspective view of a fenestrated stent.

Referring to FIG. 2, stent 20 includes a plurality of fenestrations 22 defined in a wall 23. Stent 20 includes several surface regions, including an outer, or abluminal, surface 24, an inner, adluminal, surface 26, and a plurality of cutface surfaces 28. The stent can be balloon expandable, as illustrated above, or a self-expanding stent. Examples of stents are described in Heath '721, supra.

Figure 3A:
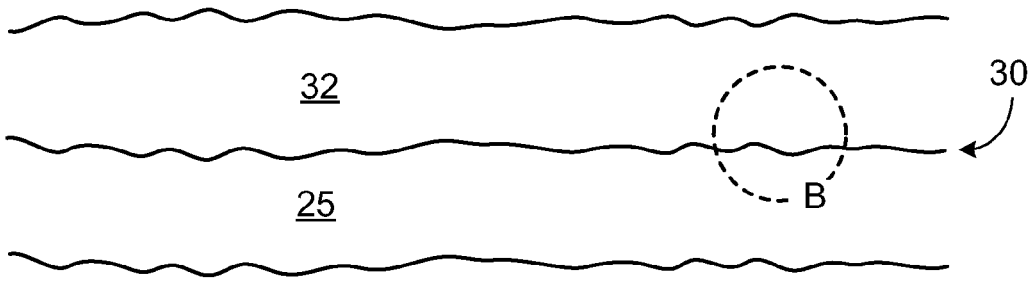
FIG. 3A is a cross-sectional view of a stent wall.

Referring to FIG. 3A, a cross-sectional view, a stent wall 23 includes a stent body 25 formed, e.g., of a polymer or a metallic material such as a metal alloy, and includes a polymeric coating 32 that includes a drug dispersed thereon and/or therein on the abluminal side. Coating 32 is bonded to stent body 25 along an interface region 30.

Figure 3B:
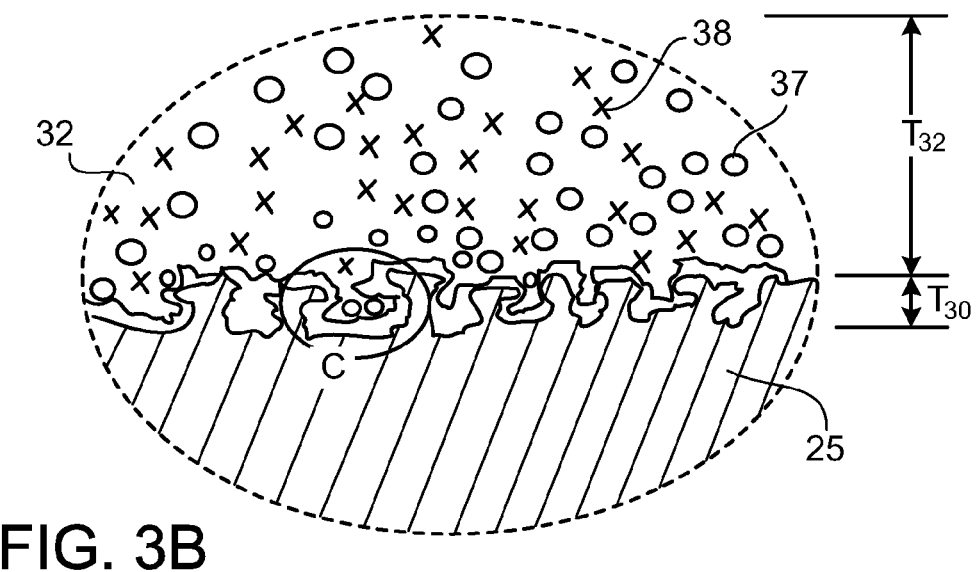
FIG. 3B is a greatly enlarged cross-sectional view of region B in FIG. 3A.
Figure 3C:
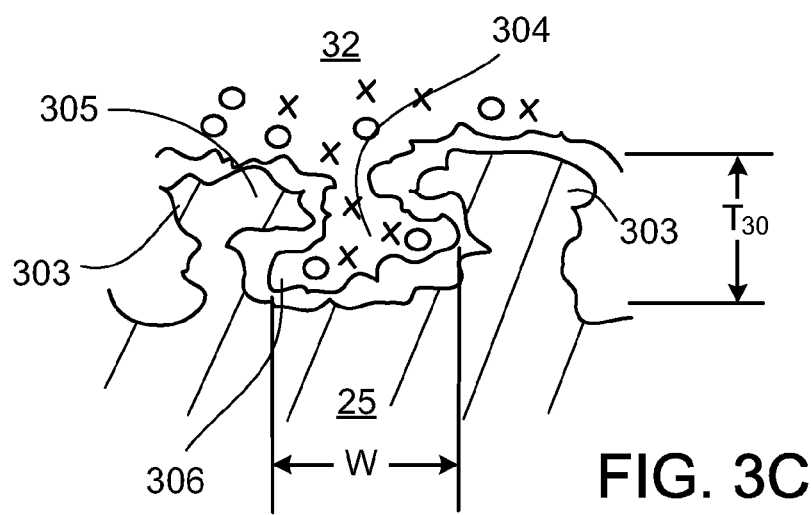
FIG. 3C is a greatly enlarged view of region C in FIG. 3B.

Referring to FIGS. 3B and 3C, at the interface region 30, surface 301 of the stent body 25 and surface 302 of the layer 32 include a plurality of defined engageable features 303, 304 such as a series of projections. In embodiments, the engageable features include overhanging projections 305, 306, similar to hooks that interengage when the surfaces are pressed together. In embodiments, the interface region, and the projections, have a thickness, $T_{30}$, of about 0.5 to 10 µm. The width, W, of the projections is about 0.5 to 20 µm, e.g. 1 to 10 µm. In embodiments, the projections on the stent and the polymer have about the same dimensions. The projections can be densely arranged so that they engage without the need for careful alignment. The engagement can be reversible, such that the polymer layer can be manually applied and removed.

Figure 4A:
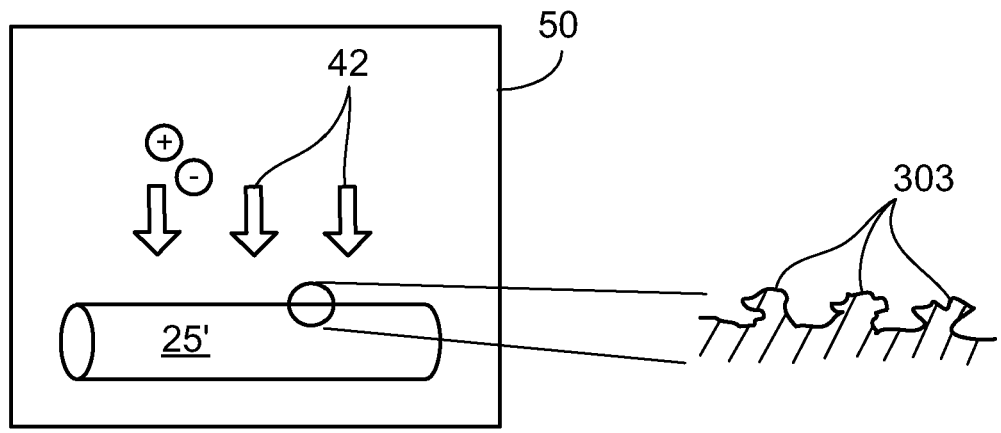
FIGS. 4A-4C are schematics illustrating a method for making a stent.
Figure 4B:
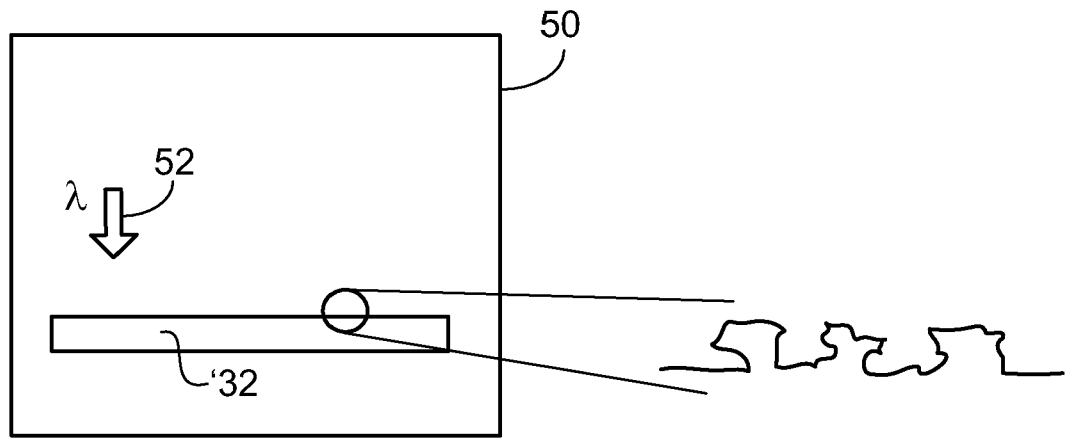
Figure 4C:
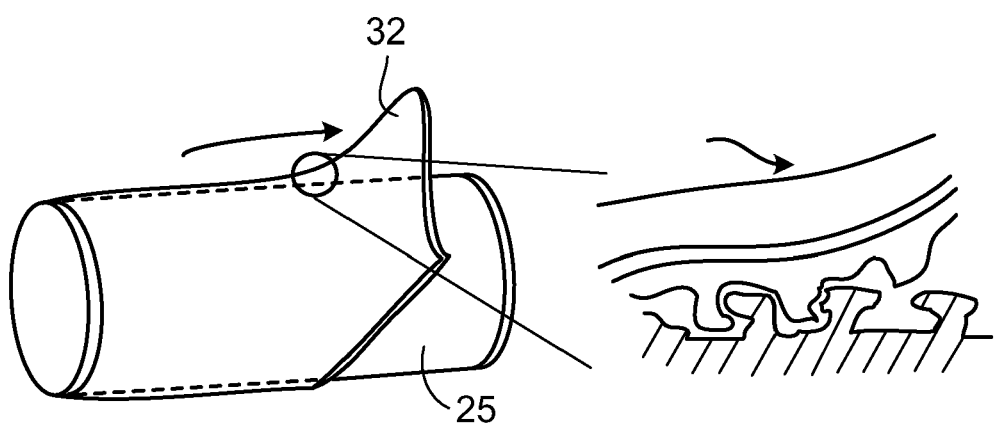

Referring to FIGS. 4A-4C, the stent is formed by separately forming engageable features on a stent substrate and a layer to be placed on the substrate, and then pressing the surfaces with engageable features together. Referring particularly to FIG. 4A, engageable features are formed on a stent or stent perform by ion bombardment. The stent or stent perform 25' is placed in a chamber 40 where it is exposed by bombardment by ions (arrows 42). The treatment provides a surface characterized by projections 303. A suitable ion bombardment technique is plasma immersion ion implantation (PIII). In some embodiments, the PIII uses noble elements, for example, argon, helium, neon, krypton, xenon, or radon. These noble elements do not react with the stent substrate and form gas bubbles within the stent substrate to create a sponge structure with openings at the surface of the stent substrate. The created sponge structure includes projections 303. The shape and size of the projections can be controlled by selection of ion type, energy level, dose rate and temperature. For example, the temperature is greater than 0.2 Tm (melting temperature of the metal). The depth of the layer being created depends on stopping power of the ions, which can be observed, or can be calculated using software available at http://www.srim.org/SRIM/History/HISTORY.htm. The actual depth of the created structure with the engageable features may be deeper than the calculated depth because of two reasons. One is that the voids created by the gas bubbles reduce the stopping power of the further impinging ions and the other is that the gas bubbles diffuse into the metal. In some embodiments, the ions have an energy level, for example, of about 10 KeV, 15 KeV, or 20 KeV, and/or up to about 60 KeV, 55 KeV, or 50 KeV. The depth of the projections can be adjusted by selecting ions with different energy levels, and different types of ions as well. Typically, argon ions creates projections with a depth in the order of micrometers and helium creates projections with a depth in the order of tens of a nanometer. For example, at a temperature of about 200° C., PIII using argon ions having an energy of about 20 KeV creates projections on the stent substrate with a depth of about 2 to 4 micrometers. Suitable ion bombardment vendors include AxynTeC (Augsburg, Germany) and Rossendorf (Dresden, Germany). The PIII technique is described in U.S. patent application Ser. Nos. 11/355,368 and 11/355,392, both filed on Feb. 16, 2006, and in U.S. Ser. Nos. 11/934,415, 11/934,342, and 11/934,421, each filed on Nov. 2, 2007. Other techniques for forming the engageable features include, for example, laser treatment, etching, and dealloying. Dealloying is discussed in Ser. No. 11/934,421, filed Nov. 2, 2007.

Referring to FIG. 4B, engageable features are formed on a layer by laser treatment. A sheet 32' of coating material is preformed, e.g. by casting or extrusion. The perform can be self-supporting or placed on a backing material, e.g. another polymer from which the sheet easily separates by peeling, solvent application, or the application of heat or light. The sheet 32' is disposed in a chamber 50 where it is exposed to laser energy (arrows 52). The treatment provides a surface on the sheet characterized by projections 304. The shape and size of the projections can be controlled by selecting the laser parameters such as wavelength, fluence, and exposure time. A suitable laser is a laser that removes polymer material by ablation. Suitable lasers include UV lasers, e.g. at 319 nm. Laser ablation to provide desirable projections is described further in Lazare et al., J. of Appl. Phys. 73, 3516-3524 (1993). Using polarized pulsed laser irradiation at fluence levels below the ablation threshold, one creates sub-micron structures in the surface of polymers. This effect is called LIPSS (laser induced periodic surface structures). The polymer is melted very briefly during the nano-second pulses. The electric field (light is an electromagnetic wave existing out of a magnetic and an electric component) which is in one direction because the polarization causes a small percentage of the polymer dipole segments to align themselves with the field during the molten phase. Repeated laser pulsing gives an incremental effect and causes the majority of the polymer dipole segments to align. A suitable wavelength of the laser is 196 nm. Laser treatments are also described in Lippert et al., 453 Chem. Rev. 2003, 103, 453-485, Wong et al., Appl. Phys. A 65, 519-523 (1997), Csete et al., Thin Solid Films 453-454 (2004) 114-120, Csetea et al., Materials Science and Engineering C 23 (2003) 939-944, and U.S. Ser. No. 11/011,454, filed Dec. 14, 2004. A drug can be loaded into the coating material before or after forming the engageable features.

Referring now to FIG. 4C, the layer 32 is assembled on the stent body 25 by pressing the surface with the engageable features on the respective surfaces together such that the features on each surface functionally engage. A single sheet of layer material can be sized to cover the entire stent or only portions of the stent surfaces can be covered. Multiple sheets, e.g. with different drugs or release rates can be used on select portions of the stent. In embodiments, the sheath and the stent can be provided as a kit, such that a physician can combine the stent and layer just prior to delivery into the body. In embodiments, heat or light can be applied after pressing to further enhance adhesion, by, e.g. melting or crosslinking.

In other embodiments, the engaging surfaces can have various other engageable features. In embodiments, the engageable features include projections and/or valleys arranged in order. In other embodiments, the engageable features include projections and/or valleys arranged in disorder. In embodiments, the engageable features include projections and/or valleys that have similar sizes and/or shapes. Generally, to have two surfaces engageable to each other, the dimensions that the engageable features of each surface has should be similar. When the morphologies of the engageable features are in small dimensions, for example, in magnitudes of about 10 nm to 100 nm, highly ordered arrangements of projections and valleys and perfect engagements are not necessary. In other embodiments, the engageable features include projections and/or valleys that have different sizes and/or shapes. Generally, when a large portion of the projections on one surface engage a large portion of the valleys on the other surface, the two surfaces engage. In embodiments, the same technique, e.g. ion bombardment or laser ablation, can be used to provide engageable features on both the stent and the layer. In embodiments, a polymer layer can be positioned on a metal stent surface by dipping or spraying. The polymer layer can be processed to form engageable structures and an additional layer, e.g. polymer or metal, with engageable structures can be assembled to the polymer layer. In some embodiments, the endoprosthesis preform can also be formed of a polymeric material. In some embodiments, laser irradiation can be used to create the engageable features on the endoprosthesis preform that is made of a polymeric material.

Figure 5A:
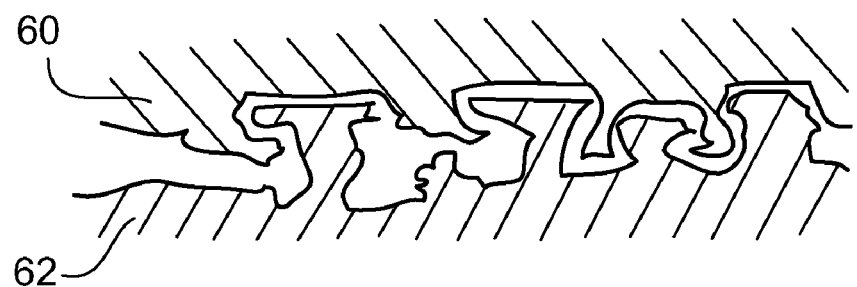
FIGS. 5A-5C are schematics illustrating delivery of a stent in a collapsed state.
Figure 5B:
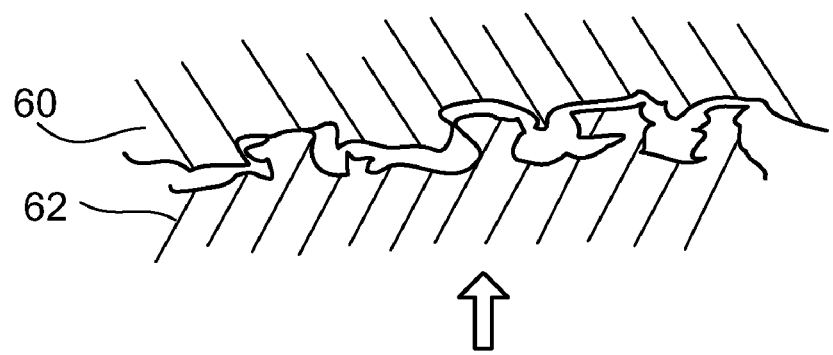
Figure 5C:
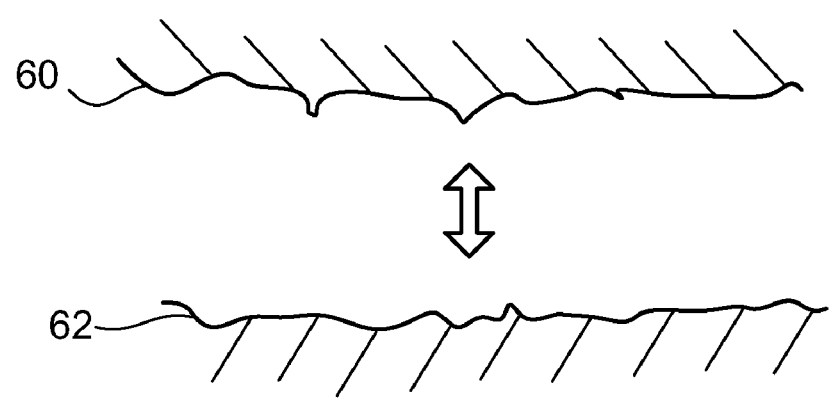

Engaging surfaces can be utilized in other medical device assemblies, such as to enhance the retention of a stent 20 on a balloon 12 during delivery into the body (FIG. 1). Referring particularly to FIGS. 5A and 5B, the luminal surface 60 of the stent and the surface 64 of the balloon both include engaging features. The engaging features help retain the stent to the balloon as the assembly is delivered through a tortuous lumen. In particular embodiments, the balloon is wing-folded and the stent is crimped on the folded balloon. As the balloon expands, the wings of the balloon unfold rotationally, releasing the engagement between the balloon and the stent. Referring to FIG. 5B, upon inflating of the balloon, the stent is expanded and the interface between the balloon and the stent is compressed under the expansion pressure (arrow). Due to the expansion of the balloon, the engagement between the balloon and the stent breaks down and the stent is dislodged. Referring to FIG. 5C, upon deflation, the force of the vacuum on the deflating balloon separates the balloon and the stent so that the catheter can be easily withdrawn.

The two surfaces can also be topologically arranged so that when they engage, the end strut of the endoprosthesis flaring can be controlled. The endoprosthesis can undergo a center up expansion when the balloon is inflated. In embodiments, the engaging elements can be arranged to reduce flaring of the axial ends of the stent relative to central portions upon expansion. Flaring might occur, for example, as the stent is expanded because the end regions expand more readily and/or the stent is axially compressed during expansion. These effects can be reduced by increasing the binding strength between the balloon and the stent at the end regions relative to the central portions. For example, the number of engaging elements on either or both of the stent and balloon can be increased in the end regions and/or the engaging elements corresponding to the end regions of either or both of the stent and balloon can be configured for greater binding strength.

The engagement mechanism can be used with other medical device assemblies. For example, for a self-expanding stent delivery system, engagement features can be provided on the stent and on the catheter body over which the stent is disposed, or on the interior surfaces of a sheath placed over the stent. The engagement mechanism can be used with catheters to deliver embolic filters and occlusion coils.

Suitable polymers include, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenerated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyiocyanates such that the devices become instantly lubricious when exposed to body fluids. In another preferred embodiment of the invention, the polymer is a copolymer of polylactic acid and polycaprolactone. Suitable polymers are discussed in U.S. Publication No. 2006/0038027.

In embodiments, the polymer is capable of absorbing a substantial amount of drug solution. When applied as a coating on a medical device in accordance with the present invention, the dry polymer is typically on the order of from about 1 to about 50 microns thick. Very thin polymer coatings, e.g., of about 0.2-0.3 microns and much thicker coatings, e.g., more than 10 microns, are also possible. Multiple layers of polymer coating can be provided. Such multiple layers are of the same or different polymer materials.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074. Polymers for drug elution coatings are also disclosed in U.S. Published Patent Application No. 2005/019265A. A functional molecule, e.g., an organic, drug, polymer, protein, DNA, and similar material can be incorporated into groves, pits, void spaces, and other features of the stent.

Any stent described herein can be dyed or rendered radiopaque by addition of, e.g., radiopaque materials such as barium sulfate, platinum or gold, or by coating with a radiopaque material. The stent can include (e.g., be manufactured from) metallic materials, such as stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stents described herein can be configured for vascular, e.g., coronary and peripheral vasculature or non-vascular lumens. For example, they can be configured for use in the esophagus or the prostate. Other lumens include biliary lumens, hepatic lumens, pancreatic lumens, urethral lumens.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., see U.S. Pat. No. 6,290,721).

All publications, patent applications, patents, the appendix, and other references mentioned herein are incorporated by reference herein in their entirety.

Still other embodiments are within the scope of the following claims.

What is claimed is:

1. An implantable medical device assembly, comprising:
   a first preformed layer member having a surface defining a plurality of preformed first engageable features;
   a second preformed layer member having a surface defining a plurality of cooperating, preformed second engageable features; and
   an interface between the first preformed layer member and second preformed layer member in which the preformed first engageable features frictionally engage with the cooperating, preformed second engageable features to form said assembly, the preformed first engageable features and the cooperating, preformed second engageable features being formed in morphologies of dimensional magnitudes of about 10-100 nm before being frictionally engaged engaging imperfectly, without a requirement of careful alignment, and with open spaces among the preformed first and second engageable features at the interface.

2. The implantable medical device assembly of claim 1, wherein at least one of the preformed first engageable features or the cooperating, preformed second engageable features comprises a plurality of overhanging projections.

3. The implantable medical device assembly of claim 2, wherein both the preformed first engageable features and the cooperating, preformed second engageable features have overhanging projections.

4. The implantable medical device assembly of claim 2, wherein the projections of the preformed first engageable features and the cooperating, preformed second engageable features have a height and width of about 0.5 to 10 µm.

5. The implantable medical device assembly of claim 1, wherein the first preformed layer member comprises a metal.

6. The implantable medical device assembly of claim 1 or claim 5, wherein the second preformed layer member is a polymer.

7. The implantable medical device assembly of claim 1, wherein both the first preformed layer member and the second preformed layer member are polymer or both the first preformed layer member and the second preformed layer member are metal.

8. The implantable medical device assembly of claim 6, wherein the polymer material includes a drug.

9. The implantable medical device assembly of claim 1, wherein the first preformed layer member is a stent body.

10. The implantable medical device assembly of claim 9, wherein the endoprosthesis is a stent including abluminal and adluminal surface regions, and wherein the first preformed layer member and the second preformed layer member and the interface are on the abluminal surface region.

11. The implantable medical device assembly of claim 10, wherein the second preformed layer member and the interface are only on the abluminal surface region.

12. The implantable medical device assembly of claim 9, wherein the stent includes multiple second preformed layer member regions at different locations over the first preformed layer member.

13. The implantable medical device assembly of claim 12, wherein the second preformed layer member regions carry different drugs or have different drug delivery profiles.

14. The implantable medical device assembly of claim 1, wherein the medical device is a stent.

15. The implantable medical device assembly of claim 1, wherein the medical device is a stent and delivery balloon.

16. The implantable medical device assembly of claim 1, wherein the second preformed layer member is a self-supporting sheet or a sheet placed on a removable backing material.

17. The implantable medical device assembly of claim 16, wherein the first preformed layer member is a stent.

* * * * *

UNITED STATES PATENT AND TRADEMARK OFFICE
CERTIFICATE OF CORRECTION

PATENT NO. : 8,114,153 B2  
APPLICATION NO. : 12/205004  
DATED : February 14, 2012  
INVENTOR(S) : Tom Holman, Jan Weber and Afsar Ali Page 1 of 1

It is certified that error appears in the above-identified patent and that said Letters Patent is hereby corrected as shown below:

Column 8, Claim 1, Line 40: after "engaged" delete "engaging".

Signed and Sealed this
Twenty-seventh Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,114,153 B2 | Page 1 of 1 |
| APPLICATION NO. | : 12/205004 | |
| DATED | : February 14, 2012 | |
| INVENTOR(S) | : Holman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 19 days.

Signed and Sealed this
Nineteenth Day of June, 2012

David J. Kappos
*Director of the United States Patent and Trademark Office*